United States Patent
Cohen et al.

(10) Patent No.: US 7,357,945 B2
(45) Date of Patent: *Apr. 15, 2008

(54) STABLE PHARMACEUTICAL FORMULATION OF PAROXETINE HYDROCHLORIDE AND A PROCESS FOR PREPARATION THEREOF

(75) Inventors: Rakefet Cohen, Zur Yigal (IL); Michael Fox, Tel-Aviv (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 79 days.

This patent is subject to a terminal disclaimer.

(21) Appl. No.: 10/891,561

(22) Filed: Jul. 14, 2004

(65) Prior Publication Data

US 2005/0059701 A1   Mar. 17, 2005

Related U.S. Application Data

(63) Continuation of application No. 10/330,616, filed on Dec. 27, 2002, now Pat. No. 7,138,137.

(60) Provisional application No. 60/344,120, filed on Dec. 28, 2001, provisional application No. 60/366,351, filed on Mar. 21, 2002.

(51) Int. Cl.
*A61K 9/20* (2006.01)
*A61K 9/28* (2006.01)

(52) U.S. Cl. .................. 424/464; 424/465; 424/474

(58) Field of Classification Search ............... 424/451, 424/464

See application file for complete search history.

(56) References Cited

U.S. PATENT DOCUMENTS

| | | | |
|---|---|---|---|
| 4,007,196 A | 2/1977 | Christensen et al. | |
| 4,721,723 A | 1/1988 | Barnes et al. | |
| 4,804,669 A * | 2/1989 | Lassen | 514/326 |
| 5,776,969 A | 7/1998 | James | |
| 6,113,944 A * | 9/2000 | Pathak et al. | 424/464 |
| 6,150,376 A | 11/2000 | Kozikowski et al. | |
| 6,168,805 B1 * | 1/2001 | Hein et al. | 424/465 |
| 6,228,864 B1 | 5/2001 | Smith et al. | |
| 6,645,523 B2 * | 11/2003 | Lemmens et al. | 424/451 |
| 2001/0008896 A1 | 7/2001 | Smith et al. | |
| 2002/0035145 A1 | 3/2002 | Tsai et al. | |
| 2002/0048600 A1 | 4/2002 | Bhatt et al. | |
| 2002/0065301 A1 | 5/2002 | Lemmens et al. | |
| 2002/0156066 A1 | 10/2002 | Chen et al. | |
| 2004/0072912 A1 | 4/2004 | Felumb et al. | |

FOREIGN PATENT DOCUMENTS

| | | | |
|---|---|---|---|
| WO | WO 00/32593 | | 6/2000 |
| WO | WO0032593 | * | 6/2000 |
| WO | WO 02/069969 | | 9/2002 |

* cited by examiner

*Primary Examiner*—Humera N. Sheikh
(74) *Attorney, Agent, or Firm*—Kenyon & Kenyon LLP

(57) ABSTRACT

Provided are formulations of a stable paroxetine hydrochloride tablet comprising paroxetine hydrochloride, povidone or copovidone as a binder, and an HCl free/non-hygroscopic filler, prepared by the wet granulation method. Preferably, the paroxetine hydrochloride is paroxetine hydrochloride hemihydrate.

13 Claims, 1 Drawing Sheet

Figure 1:
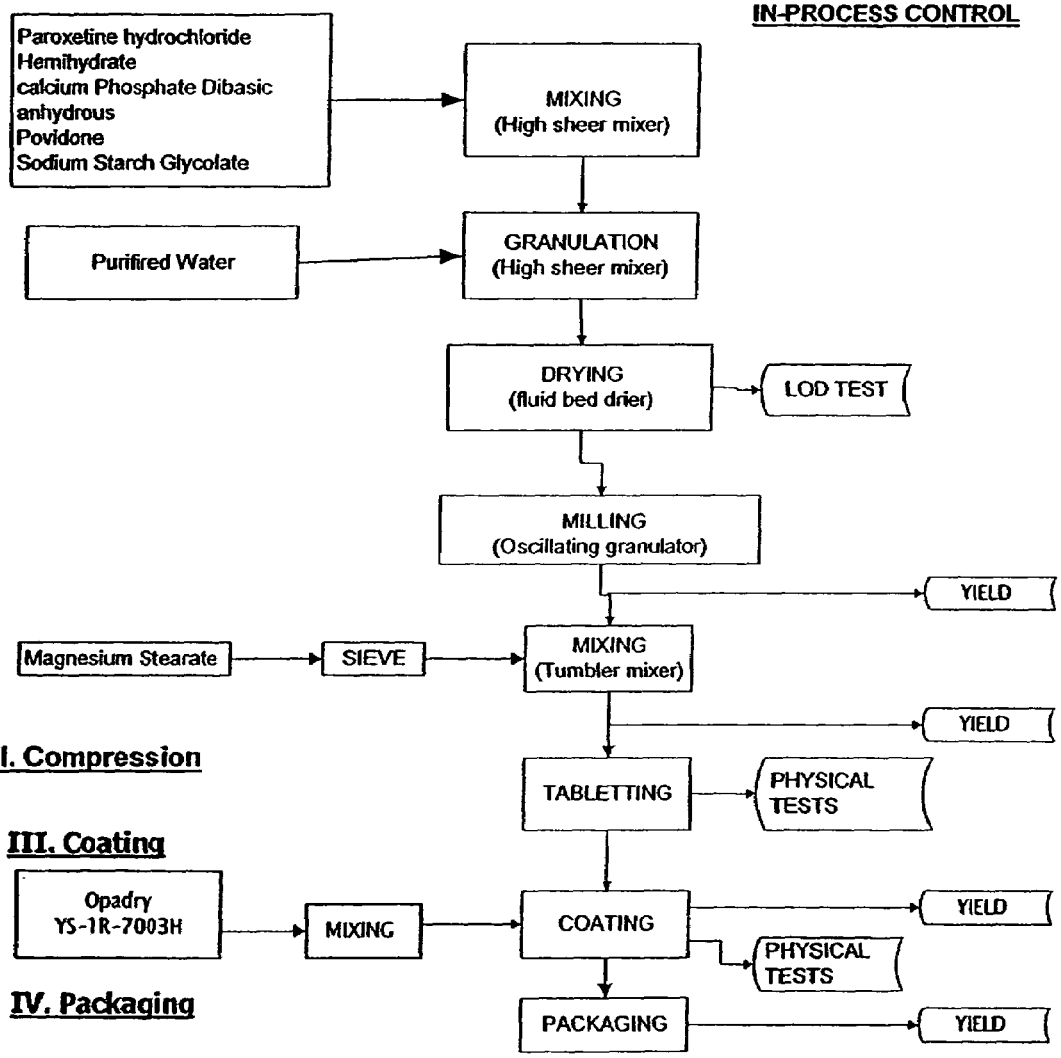

STABLE PHARMACEUTICAL FORMULATION OF PAROXETINE HYDROCHLORIDE AND A PROCESS FOR PREPARATION THEREOF

CROSS-REFERENCE TO RELATED APPLICATIONS

This application is a continuation of U.S. patent application Ser. No. 10/330,616, filed Dec. 27, 2002 now U.S. Pat. No. 7,138,137, which claims priority under 35 U.S.C. § 1.119(e) to U.S. provisional application Ser. No. 60/344,120, filed Dec. 28, 2001 and 60/366,351, filed Mar. 21, 2002. The entire content of each of these applications is incorporated herein by reference.

FIELD OF THE INVENTION

The present invention relates to pharmaceutical formulations of paroxetine hydrochloride and their preparation.

BACKGROUND OF THE INVENTION

Paroxetine, (−)-trans-3-[(1,3-benzodioxol-5-yloxy)methyl]-4-(4-fluorophenyl) piperidine; (3S, 4R)-3-[5-(1,3-dioxaindanyl)oxymethyl]-4-(p-fluorophenyl)piperidine, is a 5-hydroxytryptamine (5-HT, serotonin) re-uptake inhibitor having the formula:

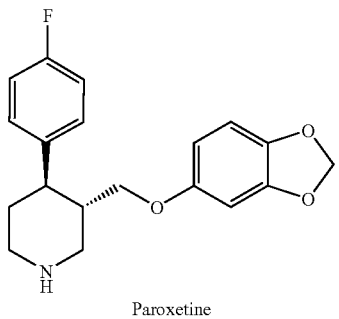

Paroxetine

Paroxetine, disclosed in U.S. Pat. No. 4,007,196 (incorporated herein by reference), is prescribed for the treatment of psychiatric problems including depression, Parkinson's disease, anxiety disorders, obsessive-compulsive disorders, panic disorder and post-traumatic stress disorder. Other syndromes such as pre-menstrual syndrome (PMS) and male sexual dysfunction can also be treated with paroxetine.

Paroxetine is marketed as Paxil® in the U.S. and as Seroxat® in other countries by GlaxoSmithKline. Paxil® is prescribed as oral dosage tablets containing 10 mg, 20 mg, 30 mg and 40 mg of the base equivalent of paroxetine hydrochloride. Paxil® tablets include dibasic calcium phosphate dihydrate, hydroxypropyl methylcellulose, magnesium stearate, polyethylene glycols, polysorbate 80, sodium starch glycolate, titanium dioxide and one or more of the following: D&C Red No. 30, D&C Yellow No. 10, FD&C Blue No. 2, FD&C Yellow No. 6.

Paxil® is also available as an oral suspension with a dosage of 10 mg of the base equivalent of paroxetine hydrochloride in a 5 mL suspension containing polacrilin potassium, microcrystalline cellulose, propylene glycol, glycerin, sorbitol, methyl paraben, propyl paraben, sodium citrate dihydrate, citric acid anhydrous, sodium saccharin, flavorings, FD&C Yellow No. 6 and simethicone emulsion, USP.

Commercial paroxetine tablets, such as Paxil® and Seroxat® contain paroxetine as paroxetine hydrochloride (HCl) hemihydrate. Although Paxil® and Seroxat® contain HPMC, it is believed that HPMC is a component of the coating in these tablets, which are probably manufactured by a direct compression method. It is believed that these tablets do not contain a binder.

Many problems are associated with paroxetine hydrochloride tablets. See e.g. WO 00/32593, incorporated herein by reference. One such problem is the susceptibility to changes in mechanical properties, particularly hardness. Paroxetine hydrochloride tablets are particularly susceptible to becoming soft during storage, especially under accelerated aging conditions. In tests performed under accelerated aging conditions, tablets of Seroxat® and those containing HPMC as a binder and microcrystalline cellulose as a filler lost a substantial amount of their hardness, more than about 40%. Thus, there is a continuing need to improve the preparation and formulations of paroxetine hydrochloride oral dosage forms, particularly tablets.

SUMMARY OF THE INVENTION

In one aspect, the present invention provides an oral pharmaceutical dosage form comprising paroxetine hydrochloride, a binder selected from the group consisting of povidone and copovidone, and a filler that is HCl free or non-hygroscopic, wherein the pharmaceutical dosage form is prepared by wet granulating paroxetine hydrochloride in the presence of a binder grade of povidone or copovidone, and the filler, to obtain an intra-granular portion of a granulate, and converting the granulate to the oral pharmaceutical dosage form.

In another aspect, the present invention provides a process for preparing an oral pharmaceutical dosage form comprising the steps of wet granulating paroxetine hydrochloride in the presence of a binder grade of a binder selected from the group consisting of povidone and copovidone, and a filler that is HCl free or non-hygroscopic, to obtain an intra-granular portion of a granulate, preparing a final blend from the granulate; and converting the final blend to an oral pharmaceutical dosage form.

In another aspect, the present invention provides for a tablet comprising of the following active ingredient and excipients, in weight to weight percentages: about 10% to about 12.5% of paroxetine hydrochloride as an active ingredient, about 70% to about 90% of dibasic calcium phosphate anhydrous, about 1.5% to about 5% of sodium starch glycolate, about 0.5% to about 3% of magnesium stearate and about 2.5% to about 7.5% of povidone, wherein the tablet is prepared by wet granulating paroxetine hydrochloride in the presence of povidone, sodium starch glycolate and dibasic calcium phosphate anhydrous to obtain a granulate, and converting the granulate to a tablet.

In another aspect, the present invention provides a process for preparing a paroxetine hydrochloride tablet comprising the steps of wet granulating with water as a processing solvent paroxetine hydrochloride in the presence of sodium starch glycolate, Grade 29 to Grade 32 povidone and dibasic calcium phosphate anhydrous, milling the granulate, mixing the granulate with an additional amount of sodium starch glycolate and calcium phosphate dibasic anhydrous, adding magnesium stearate to obtain a final blend and compressing the final blend to obtain the tablet.

In another aspect, the present invention provides for a mechanically stable paroxetine hydrochloride tablet, wherein the tablet does not substantially lose its hardness after storage at a temperature of about 80° C. and a relative humidity of at least about 75% for at least about 24 hours.

BRIEF DESCRIPTION OF THE INVENTION

FIG. 1 is a schematic diagram of a process for manufacturing paroxetine hydrochloride hemihydrate tablets.

DETAILED DESCRIPTION OF THE INVENTION

The present invention provides for stable pharmaceutical compositions of paroxetine hydrochloride and processes for their preparation. An effective amount of povidone is used in the present invention, by the wet granulation method of tablet preparation, as a binder to produce tablets that are not susceptible to losing hardness, decrease friability and/or avoid capping. Povidone's secondary effect is as a stabilizer to the mechanical properties of the tablet, especially under high temperature and/or humidity. Without wishing to be bound by any particular theory of invention or mode of action, the presence of povidone is believed to trap excess HCl present in the tablets, thus rendering the tablets stable. Additionally, the filler used during the granulation process, for optimal result, should be HCl free and/or non-hygroscopic.

Povidone, as one of skill in the art appreciates, is a synthetic water-soluble homopolymer consisting of N-vinyl pyrrolidone. It has several chemical names including 1-ethenyl-2-pyrrolidinone polymers; 1-vinyl-2-pyrrolidinone polymers; poly[1-(2-oxo-1-pyrrolidinyl)ethylene; polyvinylpyrrolidone; polyvidone; P.V.P.; RP 143, Kollidon; Peregal ST; Periston; Plasdone; Plasmosan; Protagent; Subtosan; Vinisil.

According to the *Handbook of Pharmaceutical Excipients*, published by the American pharmaceutical association, 3rd ed., povidone may be produced with an approximate molecular weight of from 2500 (grade K-12) to 3,000,000 (grade K-120). povidone K-30 has an approximate molecular weight of 50,000.

Povidone Grade K 29-32 is a universal binder. Povidone Grade K-25 has an approximate molecular weight of about 30,000. Grade K-25 is similar to Grade K 29-32, but has lower viscosity which may be advantageous in some situations. Higher grades of povidone such as K-60 or K-90, with approximate molecular weights of 400,000 and 1,000,000 respectively, are used when higher binding capacity than the K 29-32 grade is needed.

The illustrations of the present invention use a K-30 Grade povidone because it is a universal binder. One skilled in the art would appreciate that that other binder grades of povidone can also be used. Preferably, the povidone used is Grade K29 to Grade K90, more preferably Grade K29 to Grade K32, and most preferably Grade K30.

It is believed that copovidone may be used in a similar fashion in the formulations of the present invention as povidone, in approximately the same amount and viscosity disclosed herein for povidone.

If an effective amount of povidone is used in a pharmaceutical composition of paroxetine hydrochloride, the povidone imparts a stability to the pharmaceutical formulation. For optimal result, an HCl free filler or a non-hygroscopic filler, preferably a filler having both characteristics, should be used in conjunction with povidone. The paroxetine hydrochloride used can be any pseudopolymorph or polymorph of paroxetine hydrochloride, preferably paroxetine hydrochloride anhydrous or hemihydrate. These two solid state pseudopolymorph forms are differentiated by their degree of hydration. Form I is a non hygroscopic hemihydrate and is thermodynamically more stable. Form II is a hygroscopic anhydrate, and does not have water incorporated in its crystalline structure. See e.g. U.S. Pat. No. 4,721,723, incorporated herein by reference.

Preferably, the amount of povidone to paroxetine hydrochloride used is about 20% to about 60% wt/wt ratio, i.e., weight of povidone compared to weight of paroxetine hydrochloride hemihydrate. More preferably, the ratio is about 30% to about 40%, and most preferably about 35% to about 40% wt/wt ratio.

Povidone is used as an intra-granular tablet core excipient, more particularly as a binder. A tablet core excipient is an excipient used to make the core, as supposed to an excipient used in the coating process to coat the core. The granulate from which the tablet core is composed is further divided into an intra-granular and extra-granular portion. Intra-granular excipient refers to excipients added during the granulation process, while extra-granular excipients refer to excipients added after the granulation process, but before compression, or other necessary steps to convert the final blend to a desired pharmaceutical dosage form.

The amount of povidone may also be expressed in relation to the intra-granular portion. The amount of povidone to the intra-granular portion (including povidone) is preferably about 2% to about 9% w/w ratio, weight of povidone compared to the weight of intra-granular portion which includes weight of povidone. More preferably, the ratio is about 3% to about 7%, and most preferably, about 4% to about 7% weight to weight ratio.

For optimal result, the formulations of the present invention contain an HCl free filler or a non-hygroscopic filler, more preferably a filler having both characteristics. As used herein, "HCl free filler" refers to a filler that does not naturally contain and is not processed with HCl. Examples of such fillers include the sugars (e.g. lactose and mannitol, with mannitol being preferred), and more preferably dibasic calcium phosphate anhydrous. An example of a filler that includes HCl is microcrystalline cellulose, which is prepared by depolymerization of natural cellulose. The depolymerization is believed to be catalyzed by use of HCl, which results in the presence of excess HCl, and a deterioration in the final product. Microrocrystalline cellulose is also hygroscopic, i.e., a filler that absorbs water from its surrounding.

In addition to a binder and a filler, the pharmaceutical compositions of the present invention can include other excipients known in the art, both for the tablet core and coating. For example, the dissolution rate of a compacted solid pharmaceutical composition in the patient's stomach may be increased by the addition of a disintegrant to the composition. Disintegrants include for example alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Suitable lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Glidants for example can be added to improve the flow properties of non-compacted solid composition and improve the accuracy of dosing. Excipients that may function as glidants include for example colloidal silicon dixoide, magnesium trisilicate, powdered cellulose, starch, talc and tribasic calcium phosphate.

Another class of excipients is flavoring agents and flavor enhancers make the dosage form more palatable to the patient. Common flavoring agents and flavor enhancers for pharmaceutical products include for example maltol, vanillin, ethyl vanillin, menthol, citric acid, fumaric acid, ethyl maltol, and tartaric acid. Various coloring agents can also be used.

The oral pharmaceutical dosage forms of the present invention are prepared by wet granulating paroxetine hydrochloride in the presence of a binder grade of a binder selected from the group consisting of povidone and copovidone, and a filler that is HCl free or non-hygroscopic, to obtain an intra-granular portion of a granulate, preparing a final blend from the granulate and converting the final blend to an oral pharmaceutical dosage form. The oral pharmaceutical dosage forms of the present invention, in addition to tablets, may be in the form of tablets, capsules, sachets, granules, suspension, effervescent tablets, chewable tablets and geltabs.

The term wet granulation refers to granulation in the presence of an aqueous processing solvent, as supposed to granulation in the absence of any processing solvent or a non-aqueous processing solvent. Preferably, the processing solvent of the wet granulation is water or a mixture of water and another water miscible solvent. Examples of such water miscible solvents include $C_1$ to $C_3$ alcohols and lower ketones. Preferred solvent mixtures include: water and acetone; water and methanol; water and ethanol; and water, methanol/ethanol and acetone.

In one embodiment illustrated by the examples, paroxetine hydrochloride hemihydrate, a filler, preferably calcium phosphate anhydrous, a disintegrant, preferably sodium starch glycolate and an effective amount of povidone are mixed together. A high sheer mixer known in the art can be used. Water is then added to the mixer to start the wet granulation process. After the granulation process, the granulate can be milled to obtain a granulate of a desired size. Additional amounts of filler and disintegrant can be added, while using a mixer, preferably a tumbler mixer. The excipients added after granulation can be of the same or different quality/grade of the same excipient used during the granulation process. After the wet granulation, the granulate is preferably dried to an LOD of about NMT 1%.

Preferably, a lubricant, such as magnesium stearate is added to obtain a final blend.

The resulting final blend is then compressed into a tablet. A preferred tablet comprises of the following active ingredient and excipients, in weight to weight ratios: about 10 to about 12.5% of paroxetine hydrochloride, about 70% to about 90% of dibasic calcium phosphate, about 1.5% to about 5% of sodium starch glycolate, about 0.5% to about 3% of magnesium stearate and about 2.5% to about 7.5% of povidone. Preferably, the paroxetine hydrochloride is paroxetine hydrochloride hemihydrate.

In one embodiment, the tablet coat is coated, more preferably by using opadry® (Colorcon, Westpoint Pa.). According to Colorcon, Opadry® is a one-step customized coating system that combines polymer, plasticizer, and if desired, a pigment in dry concentrate. Preferably, the coating used for the tablets includes about 25% to about 35%, more preferably 30% titanium dioxide, about 25% to about 35%, more preferably about 30% hydroxypropyl methylcellulose, preferably about 5% to about 10%, more preferably about 8% polyethylene glycol and preferably about less than 1% to about 3%, more preferably about 1 percent polysorbate, respective weight to weight. Preferably, about 3 mg to about 12 mg of the coating is used.

The presence of an effective amount of povidone and an HCl free/non-hygroscopic filler renders the pharmaceutical compositions of the present invention stable, and resistant to mechanical change, particularly to becoming soft overtime. The paroxetine hydrochloride hemihydrate tablets are stable in that they do not substantilly lose their hardness under accelarated aging conditions, i.e., a loss of more than about 40% in hardness under accelarated aging conditions. As the examples illustrate, the paroxetine hydrochloride hemihydrate tablet of the present invention did not lose any hardness under such aging conditions, and retained a hardness of at least about 16 SCU. Preferably less than about 20% of hardness, more preferably less than about 10%, and most preferably no noticeable loss of hardness occurrs. This substantial lack of mechanical change is in contrast with Seroxat® which loses about half of its hardness under identical accelarated aging conditions.

Preferably, a stable paroxetine hydrochloride tablet retains a hardness value of at least about 10 SCU after about 24 hours of storage at about 80° C. and at least about 75% relative humidity. More preferably, the hardness is at least about 12 SCU, even more preferably at least about 14 SCU, and most preferably at least about 16 SCU.

Optimal unit dosages of paroxetine hydrochloride can be made for effective inhibition of serotonin re-uptake. The unit dosages of parxetine hydrochloride are preferably no more than about 100 mg, more preferably no more than about 50 mg, and most preferably about 10 mg, 20 mg, 30 mg and 40 mg of the base equivalent of paroxetine hydrochloride. The following non-limiting examples further illustrate the embodiments of the invention.

EXAMPLES

Example 1

Preparation of a Stable Tablet of Paroxetine Hydrochloride Hemihydrate

A. The Process

A schematic for preparing stable tablets of paroxetine hydrochloride is shown in FIG. 1. Active ingredient paroxetine hydrochloride hemihydrate was mixed with dibasic anhydrous calcium phosphate, sodium starch glycolate and an effective amount of povidone binder. A wet granulation method was used to prepare a tableting mixture that was pressed into tablets.

Coating was achieved using Opadry®.

B. The Composition

The paroxetine hydrochloride hemihydrate tablet was prepared using about 20 mg of paroxetine hydrochloride hemihydrate and 8 mg of povidone per tablet, and its composition is provided in Table 1.

TABLE 1

Tablet Composition of Paroxetine Hydrochloride Hemihydrate
[Includes extra-granular excipients]:

| INGREDIENTS | Mg per tablet | FUNCTION |
|---|---|---|
| Cores | | |
| Paroxetine Hydrochloride Hemihydrate | 22.76 | Active Ingredient |
| Dibasic Calcium Phosphate Anhydrous | 160.24 | Filler |
| Povidone (PVP K-30) | 8.0 | Binder |
| Sodium starch Glycolate | 6.0 | Disintegrant |
| Magnesium Stearate | 3.0 | Lubricant |
| Purified water | Q.S. (Quantum Satis) | Processing solvent (wet granulation) |
| Coating Suspension: | | |
| *Opadry ® | 6.0 | |

| *Composition of the Opadry ® | % W/W |
|---|---|
| Titanium Dioxide | 31.250 |
| Hydroxypropyl methylcellulose (Methocel E3 Premium) | 29.875 |
| Hydropropyl methylcellulose (Methocel E5 Premium) | 29.875 |
| Polyethylene Glycol 400 | 8.000 |
| Polysorbate 80 (Tween) | 1.000 |

Example 2

Comparative Mechanical Analysis Of Parxetine Hydrochloride Hemihydrate Tablets

A tablet of Seroxat®, a 20 mg tablet containing hydroxypropyl methylcellulose as a binder and the tablet prepared in example 1 were tested for hardness under accelerated aging conditions after 24 hours.

TABLE 2

Hardness Test of the Paroxetine Hydrochloride Hemihydrate Tablets- (Kraemer ® Tablets Test System)

| PRODUCT | HARDNESS OF THE TABLETS, SCU INITIAL | HARDNESS OF THE TABLETS, SCU AFTER 24 HOURS, 80° C., 75% RELATIVE HUMIDITY |
|---|---|---|
| Commercial product-Seroxat ® 20 mg | 15 | 8 |
| Binder-Hydroxypropyl Methylcellulose Filler-Avicel and dibasic calcium phosphate anhydrous | 10 | 6 |
| Binder-povidone K-30 Filler-dibasic calcium phosphate anhydrous [As prepared in Example 1] | 16 | 17 |

Example 3

Preparation of a Stable Tablet of Paroxetine Hydeochloride Hemihydrate

A paroxetine hydrochloride hemihydrate tablet was prepared using about 20 mg of paroxetine hydrochloride hemihydrate and 8 mg of povidone:

a) Paroxetine hydrochloride hemihydrate, dibasic calcium phosphate anhydrous, sodium strach glycolate and povidone were premixed and granulated with water;

b) The granulate, after drying and milling through a 0.6 mm sieve, was mixed with dibasic calcium phosphate anhydrous and sodium starch glycolate in a dry state for 20 minutes. Then magnesium stearate was added, followed by mixing for a further 5 minutes;

c) Tablets were pressed from the resulting mixture, and coated with a coating suspension of Opadry®.

Tablet weight was for about 20 mg strength; Approximately 206 milligrams.

TABLE 3

Tablet Composition of Paroxetine Hydrochloride Hemihydrate:

| INGREDIENTS | Percent by weight |
|---|---|
| Intra-Granular core | |
| Paroxetine Hydrochloride Hemihydrate | 11.0 |
| Dibasic Calcium Phosphate Anhydrous (fine powder) | 46.7 |
| Povidone (PVP K-30) | 3.9 |
| Sodium Starch Glycolate | 6.0 |
| Extra-Granular Core | |
| Magnesium Stearate | 1.5 |
| Dibasic Calcium Phosphate Anhydrous DC Grade | 31.1 |
| Sodium Starch Glycolate | 1.0 |
| Coating: | |
| Opadry ® YS-1-7003H | 3.0 |

TABLE 2

Hardness Test of the Paroxetine Hydrochloride Hemihydrate Tablets- (Kraemer ® Tablets Test System)

| HARDNESS OF THE TABLETS, SCU INITIAL | HARDNESS OF THE TABLETS, SCU AFTER 24 HOURS, 80° C., 75% RELATIVE HUMIDITY |
|---|---|
| 16 | 18 |

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of excipients are disclosed for example in *Handbook of Pharmaceutical Excipients*, published by the American pharmaceutical association, 3rd ed. All references mentioned herein are incorporated in their entirety.

What is claimed is:

1. A tablet comprising of the following active ingredient and excipients, in weight to weight percentages:
   a) about 10% to about 12.5% of paroxetine hydrochloride as an active ingredient;
   b) about 70% to about 90% of dibasic calcium phosphate anhydrous;
   c) about 1.5% to about 5% of sodium starch glycolate;
   d) about 0.5% to about 3% of magnesium stearate; and
   e) about 2.5% to about 7.5% of povidone,
   wherein the tablet is prepared by wet granulating paroxetine hydrochloride in the presence of povidone, sodium starch glycolate and dibasic calcium phosphate anhydrous to obtain a granulate, and converting the granulate to a tablet.

2. The tablet of claim 1, wherein the paroxetine hydrochloride is paroxetine hydrochloride hemihydrate.

3. The tablet of claim 1, further comprising about 3 to about 12 mg of a coating composition of about 30% titanium dioxide, about 30% hydroxypropyl methylcellulose, about 8% polyethylene glycol and about 1% polysorbate, respective weight to weight.

4. The tablet of claim 1, wherein the wet granulating is carried out with water as a processing solvent.

5. The tablet of claim 1, wherein the wet granulating is carried out with a mixture of water and a water miscible ketone or alcohol, or mixtures thereof as a processing solvent.

6. A method for inhibiting the re-uptake of serotonin comprising administering the tablet of claim 1 to a mammal.

7. A process for preparing a paroxetine hydrochloride tablet comprising the steps of:
   a) wet granulating with water as a processing solvent paroxetine hydrochloride in the presence of sodium starch glycolate, Grade 29 to Grade 32 povidone and dibasic calcium phosphate anhydrous to obtain an intragranular portion;
   b) milling the intragranular portion;
   c) mixing the intragranular portion with an additional amount of sodium starchglycolate and calcium phosphate dibasic anhydrous;
   d) adding magnesium stearate to obtain a final blend; and
   e) compressing the final blend to obtain the tablet,
   wherein the ratio of povidone or to paroxetine hydrochloride is from about 20% to about 60% weight to weight of povidone to paroxetine hydrochloride or wherein the ratio of povidone to the intra-granular portion is about 2% to about 9% weight to weight of povidone to intra-granular portion, the intra-granular weight including the weight of povidone.

8. The process of claim 7, wherein the paroxetine hydrochloride is paroxetine hydrochloride hemihydrate.

9. A tablet comprising of the following active ingredient and excipients, in weight to weight percentages:
   a) about 10% to about 12.5% of paroxetine hydrochloride as an active ingredient;
   b) about 70% to about 90% of dibasic calcium phosphate anhydrous;
   c) about 1.5% to about 5% of sodium starch glycolate;
   d) about 0.5% to about 3% of magnesium stearate; and
   e) about 2.5% to about 7.5% of povidone, wherein the tablet does not substantially lose its hardness after storage at a temperature of about 80° C. and a relative humidity of at least about 75% for at least about 24 hours.

10. The tablet of claim 9, wherein the paroxetine hydrochloride is paroxetine hydrochloride hemihydrate.

11. The tablet of claim 9, further comprising about 3 to about 12 mg of a coating composition of about 30% titanium dioxide, about 30% hydroxypropyl methylcellulose, about 8% polyethylene glycol and about 1% polysorbate, respective weight to weight.

12. The tablet of claim 9, wherein the wet granulating is carried out with water as a processing solvent.

13. The tablet of claim 9, wherein the wet granulating is carried out with a mixture of water and a water miscible ketone or alcohol, or mixtures thereof as a processing solvent.

* * * * *